(12) United States Patent
Jeong et al.

(10) Patent No.: US 11,733,226 B2
(45) Date of Patent: Aug. 22, 2023

(54) AIR STATE DETECTION FLOATING DEVICE CAPABLE OF REMAINING IN AIR

(71) Applicant: NATIONAL DISASTER MANAGEMENT INSTITUTE, Ulsan (KR)

(72) Inventors: Gun Sik Jeong, Ulsan (KR); KyungSu Lee, Ulsan (KR); Sung Geun Bae, Ulsan (KR); Da jin sol Kim, Ulsan (KR); Tae Wook Lee, Ulsan (KR); Hyunju Kim, Ulsan (KR)

(73) Assignee: NATIONAL DISASTER MANAGEMENT INSTITUTE, Ulsan (KR)

( * ) Notice: Subject to any disclaimer, the term of this patent is extended or adjusted under 35 U.S.C. 154(b) by 375 days.

(21) Appl. No.: 16/612,862

(22) PCT Filed: Nov. 1, 2018

(86) PCT No.: PCT/KR2018/013147
§ 371 (c)(1),
(2) Date: Nov. 12, 2019

(87) PCT Pub. No.: WO2019/117458
PCT Pub. Date: Jun. 20, 2019

(65) Prior Publication Data
US 2020/0182846 A1    Jun. 11, 2020

(30) Foreign Application Priority Data
Dec. 15, 2017  (KR) .......................... 10-2017-0173291

(51) Int. Cl.
*G01N 33/00* (2006.01)
*G05B 15/02* (2006.01)

(52) U.S. Cl.
CPC ..... *G01N 33/0062* (2013.01); *G01N 33/0027* (2013.01); *G05B 15/02* (2013.01)

(58) Field of Classification Search
CPC .. G01N 33/0062; G01N 33/0027; G01N 1/22; G01N 1/2273; G01N 2001/2276;
(Continued)

(56) References Cited

U.S. PATENT DOCUMENTS

2016/0290912 A1* 10/2016 Kent .................. G01N 15/0612
2017/0187993 A1   6/2017 Martch et al.
2017/0336381 A1* 11/2017 Zeevi .................... G01N 29/02

FOREIGN PATENT DOCUMENTS

CN    106770976    *  5/2017
DE    10122139     * 11/2002
(Continued)

OTHER PUBLICATIONS

International Search Report of PCT/KR2018/013147, dated Feb. 1, 2019, English translation.

*Primary Examiner* — Robert R Raevis
(74) *Attorney, Agent, or Firm* — STIP Law Group, LLC (57) ABSTRACT

A device can provide an air state detection floating device capable of remaining in the air, the device comprising: a power supply unit; at least one memory for storing instructions; at least one processor; a communication unit for transmitting and receiving data; a driving unit for generating a driving force; a first sensing unit for detecting information on an air state of an enclosed space; and a second sensing unit for generating location information, wherein the instructions are executable by the processor so as to the processor to perform operations, and the operations comprise: an operation that generates a control signal for move- (Continued)

ment in the enclosed space on the basis of the data; and an operation that controls the driving unit based on the control signal.

8 Claims, 8 Drawing Sheets

(58) Field of Classification Search
CPC ............. G01N 33/0004; G01N 33/227; G01N 2201/0214; G01N 2001/2229; G05B 15/02
USPC ...... 73/23.2, 23.3, 23.34, 31.01, 31.02, 488, 73/493, 864.34, 864.81, 865.8
See application file for complete search history.

(56) References Cited

FOREIGN PATENT DOCUMENTS

| JP | 2002255096 A | 9/2002 |
| JP | 2013189036 A | 9/2013 |
| JP | 2017109593 A | 6/2017 |
| KR | 1020110053826 A | 5/2011 |
| KR | 1020160098807 A | 8/2016 |
| KR | 1020170025794 A | 3/2017 |
| WO | WO2012091489 A2 | 7/2012 |
| WO | 2016201113 | * 12/2016 |

* cited by examiner

AIR STATE DETECTION FLOATING DEVICE CAPABLE OF REMAINING IN AIR

CROSS-REFERENCE TO RELATED APPLICATIONS

This application is the U.S. National Phase under 35 U.S.C. § 371 of International Application No. PCT/KR2018/013147 filed on Nov. 1, 2018, which in turn claims the benefit of Korean Application No. 10-2017-0173291, filed on Dec. 15, 2017, the disclosures of which are incorporated by reference into the present application.

BACKGROUND

Technical Field

The present disclosure generally relates to an air state detection floating device capable of remaining in air, and specifically, to a device which is capable of floating and remaining in air in an enclosed space.

Related Art

An enclosed space refers to a place where workers can perform work with insufficient ventilation, such as wells, vertical shafts, tunnels, caissons, culverts, manholes, tanks, reactors, septic tanks, settling tanks, sump tanks, etc. In a case where a worker performs the work in such a confined space, oxygen cannot normally be supplied to the worker's body and an accident may occur due to suffocation. In particular, occasionally when a worker enters a place that lacks oxygen, he/she may collapse and die in less than a few minutes without being aware of the risk of suffocation. Additionally, in an enclosed space where ventilation is not sufficient, there may be harmful gases which cause a smothering action due to the poisoning of the body in addition to oxygen deficiency. Since these harmful gases cause a smothering action when the body is exposed to these harmful gases even when the oxygen concentration is in a state of normal concentration, it is necessary to confirm not only the oxygen concentration but also the concentrations of possible harmful gases in a place where there is a risk of generation of these gases.

In this regard, KR Patent Application Publication No. 10-2011-0053826 discloses a complex network system and method for safe monitoring of the harmful workshop. However, the harmful reduction sensing device in prior art employs a method where the device is fixedly attached to a harmful workplace, and thus there is a limitation in that the device cannot perform its function due to malfunction or failure of the device by the submerging of the device depending on the level of the enclosed space in the enclosed space in which liquid materials are present (e.g., a septic tank).

SUMMARY

The present disclosure has been made to solve the above-mentioned conventional problems. An object of the present disclosure is to provide a device which can detect the air state in an enclosed space while flying within the enclosed space and can detect air state on the water surface regardless of the level of the liquids in an enclosed space.

An embodiment may provide an air state detection floating device capable of remaining in the air, the device including: a power supply unit; at least one memory for storing instructions; at least one processor; a communication unit for transmitting and receiving data; a driving unit for generating a driving force; a first sensing unit for detecting information on an air state of an enclosed space; and a second sensing unit for generating location information, wherein the instructions are executable by the processor so as to the processor to perform operations, and the operations include: an operation that generates a control signal for movement in the enclosed space on the basis of the data; and an operation that controls the driving unit based on the control signal.

Another embodiment may provide an air state detection floating device capable of remaining in the air, in which the communication unit transmits and receives the data with a station installed in the enclosed space, and the power supply unit receives power from the station.

Still another embodiment may provide an air state detection floating device capable of remaining in the air, in which the operations further include an operation which controls the first sensing unit based on the detection results of the second sensing unit.

Still another embodiment may provide an air state detection floating device capable of remaining in the air, in which the operations further include: an operation, which monitors charging power of the power supply unit; an operation, which sets a return path based on preset route information when the charging power is lower than the preset value; an operation, which controls the operation unit based on the return path; and an operation, which is docking with the station and charges the power supply unit using the power received from the station.

Still another embodiment may provide an air state detection floating device capable of remaining in the air, in which, at the time of docking with the station, a magnetic force formed in the station is used.

Still another embodiment may provide an air state detection floating device capable of remaining in the air, in which the device further includes a case for accommodating the power supply unit, the memory, the processor, the communication unit, the operation unit, the first sensing unit, and the second sensing unit; and a buoyancy supply unit for providing buoyancy to the case.

Still another embodiment may provide an air state detection floating device capable of remaining in the air, in which the device further includes an air suction device, which sucks air in the enclosed space installed in the case; and an air exhaust device, which exhausts the sucked air; wherein the operations further include an operation, which controls a first sensing unit for detecting the state of the air introduced into the air suction device, the air exhaust device, and the air suction device, based on the detection results of the second sensing unit.

Still another embodiment may provide an air state detection floating device capable of remaining in the air, in which the device further includes a flight driving device that provides flight power.

Still another embodiment may provide an air state detection floating device capable of remaining in the air, in which the device further includes a flight driving device which is controlled by the driving unit and is attachable to and detachable from the case.

Still another embodiment may provide an air state detection floating device capable of remaining in the air, in which the operations further include an operation, which generates a control signal based on the path information that is previously recorded in the memory and responds to the spatial information in the enclosed space, and thereby controls the driving unit.

Still another embodiment may provide an air state detection floating device capable of remaining in the air, in which the device further includes a protective case that surrounds the air state detection floating device capable of remaining in air and the flight driving device, and is coupled to the air state detection floating device capable of remaining in air, wherein the protective case has a mesh-type structure.

DESCRIPTION OF EXEMPLARY EMBODIMENTS

Since various modifications can be made to the present disclosure and various embodiments thereof are available, specific embodiments will be illustrated in the drawings and described in detail in the detailed description. The effects and features of the present disclosure and methods of achieving them will be apparent with reference to the embodiments described in detail below with reference to the drawings. However, the present disclosure is not limited to the embodiments disclosed hereinbelow, but it may be implemented in various forms. In the embodiments below, the terms such as first, second, etc. are used for the purpose of distinguishing one element from another element. Additionally, the singular expression may include a plural expression unless the context clearly specifies otherwise. Additionally, the terms such as comprising or having means that a feature or element described in the specification is present, and it does not exclude the possibility that one or more other features or components may be added. Additionally, in the drawings, components may be exaggerated or reduced in size for convenience of explanation. For example, the size and thickness of each component shown in the drawings are arbitrarily shown for convenience of explanation, and thus the present disclosure is not necessarily limited to those illustrated.

Hereinafter, exemplary embodiments of the present disclosure will be described in detail with reference to the accompanying drawings, in which in describing the drawings, the same or corresponding components are denoted by the same reference numerals throughout the drawings and a duplicate description thereof will be omitted.

Figure 1:
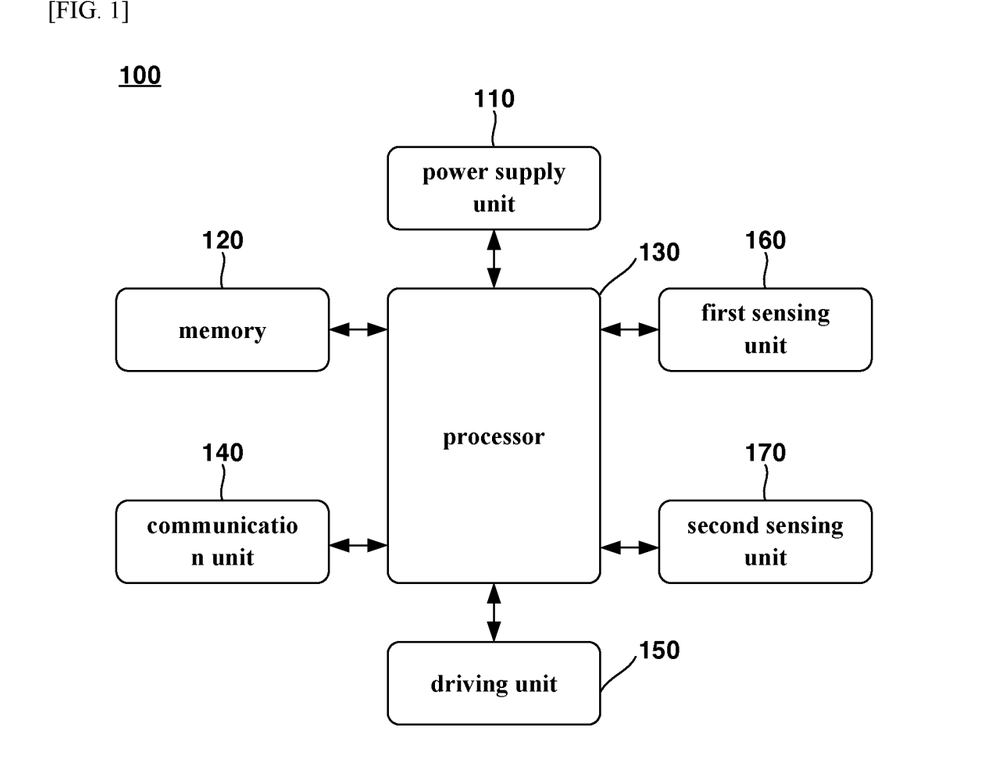
FIG. 1 is an exemplary block diagram according to an embodiment of the present disclosure.
Figure 2:
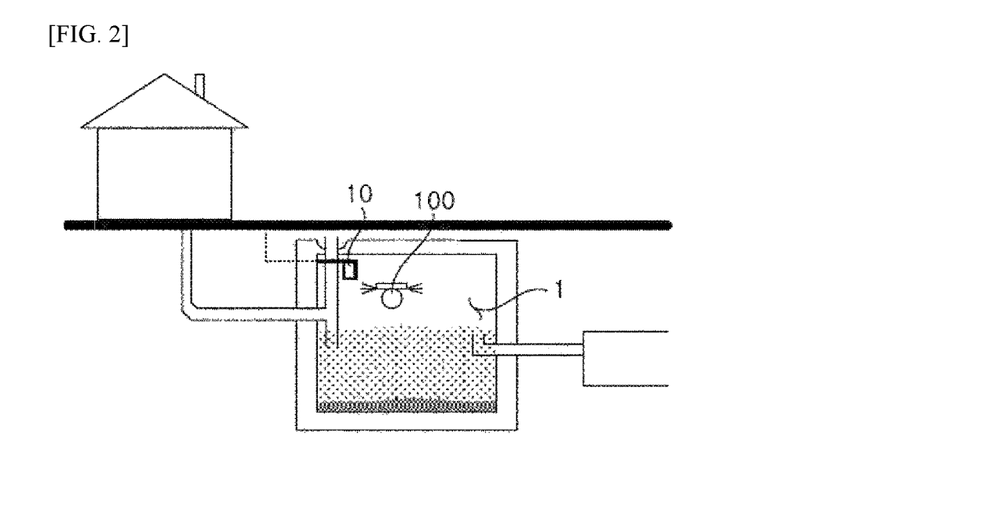
FIG. 2 exemplarily illustrates an environment in an enclosed space to which an embodiment of the present disclosure is applied.

FIG. 1 is an exemplary block diagram according to an embodiment of the present disclosure; and FIG. 2 exemplarily illustrates an environment in an enclosed space to which an embodiment of the present disclosure is applied.

In explaining the present disclosure, the term "enclosed space" refers to a place where workers can perform work, in which risks of oxygen deficiency, a health hazard caused by harmful gases, fire or explosion due to flammable materials, etc. are present in a state of insufficient ventilation. Generally, these places may include wells, vertical shafts, tunnels, caissons, pits, culverts, manholes, tanks, reactors, septic tanks, settling tanks, sump tanks, etc., but the places are not limited thereto and any space may be applied as long as it is a space in which liquids are present, the ventilation is not sufficient and the water level therein is expected to fluctuate.

Embodiments of the present disclosure can detect the concentrations of various gases including harmful gases and oxygen in an enclosed space. In connection with the detection of harmful gases, harmful gases that cause the smothering action due to the poisoning of the body may be present in the enclosed, in which ventilation is insufficient. These harmful gases are called chemical asphyxiants and their representative materials include carbon monoxide, hydrogen sulfide, methylene chloride, cyanide, etc. These harmful gases can cause a smothering action when exposed to the human body even under a normal oxygen concentration, and thus it is important to check the detection and concentrations of possible harmful gases that can be generated in an enclosed where it is highly likely that these harmful gases may be generated. Additionally, in connection with the detection of oxygen concentration, in a case where the enclosed space 1 is an internal space of a steel tank, if there is water in the steel tank or the steel tank is sealed for a long period of time, the rust formed by oxidation of the internal wall can reduce the oxygen in the tank causing a state of oxygen deficiency, and may become a state of oxygen deficiency according to the rancidity of dry oil, respiration of microorganisms, and oxidation of stored products within the enclosed space. In this case, breathing air with an oxygen concentration of less than 16% will result in a lack of oxygen in the body tissue and acceleration of pulse and respiration rates thus showing symptoms such as vomiting and headache, whereas breathing air with the oxygen concentration of less than 16% will result in a loss of consciousness, seizure, decrease of blood pressure, and decrease in the number of pulsation, and thus the detection of oxygen concentration within the enclosed space 1 is important.

Referring to FIGS. 1 and 2, the air state detection floating device capable of remaining in air 100 according to an embodiment of the present disclosure may include a power supply unit 110, at least one memory for storing instructions 120, at least one processor 130, a communication unit for transmitting and receiving data 140, a driving unit 150 for generating a driving force, a first sensing unit 160 for detecting information on an air state of an enclosed space, and a second sensing unit 170 for generating location information.

The power supply unit 110 can be charged by receiving power from a station 10 by wire or wirelessly. The power supply unit 110 can receive power provided by the station 10 when the device 100 and the station 10 are electrically coupled to each other. The power supply unit 110 may consist of a power control unit and a battery. The power control unit 111 can control the charging power of the battery 112 and can detect information on the charging state of the battery 112. The power supply unit 110 can provide the power necessary to perform overall operations, such as movement of the device 100, air state detection, and data transmission and reception.

The memory 120 may include one or more computer-readable storage media. Computer-readable storage medium is tangible and non-transitory. The memory 120 can include a fast random access memory, and in addition, may include a non-volatile memory (e.g., one or more magnetic disk storage devices, flash memory devices, other non-volatile solid-state memory devices, etc.). A memory controller can control the access to the memory 120 by other components of the device 100.

The processor 130 may be configured in various forms, such as one or more microprocessors, digital signal processors (DSPs), application-specific integrated circuits (ASICs), field programmable gate arrays (FPGAs), individual logic circuits, software, hardware, firmware, or any combination thereof.

The communication unit 140 may consist of a radio frequency (RF) circuit. The communication unit 140 can receive and transmit RF signals, which is also called electromagnetic signals. The communication unit 140 converts an electrical signal into an electromagnetic signal and/or converts an electromagnetic signal into an electrical signal; and communicates with the communication network and a communication device of the station 10 through the electromagnetic signal. The communication unit 140, as an option, includes a known circuit to perform the functions of those which include, but is not limited to, an antenna system, an RF transceiver, one or more amplifiers, a tuner, one or more oscillators, a digital signal processor, a CODEC chipset, a Subscriber Identity Module (SIM) card, a memory, etc. The communication unit 140, as an option, can communicate by wireless communication with networks, such as the "internet", also referred to as "world wide web" (WWW), a wireless network such as an intranet and/or cellular telephone network, a wireless local area network (LAN) and/or a metropolitan area network (MAN), and devices of the station 10. The communication unit 140, as an option, can include a known circuit for detecting near field communication (NFC) fields, such as a short range wireless device, etc. The wireless communication, as an option, can use any of those which include a plurality of communication standards, protocols, and techniques, which includes, but is not limited to. "global system for mobile communications (GSMs)", enhanced data GSM environment (EDGE), high-speed downlink packet access (HSDPA), high-speed uplink packet access (HSDPA), evolution, data-only (EV-DO), HSPA, HSPA+, dual-cell HSPA (DCHSPDA), long term evolution (LTE), near field communication (NFC), wideband code division multiple access (W-CDMA), code division multiple access (CDMA), time division multiple access (TDMA), bluetooth, bluetooth low energy (BTLE), wireless fidelity (Wi-Fi) (e.g., IEEE 802.11a, IEEE 802.11b, IEEE 802.11g, IEEE 802.11n, and/or IEEE 802.11ac), voice over internet protocol (VoIP), Wi-MAX, protocol for e-mails (e.g., internet message access protocol (IMAP) and/or post office protocol (POP)), instant messaging (e.g., extensible messaging and presence protocol (XMPP), session initiation protocol for instant messaging and presence leveraging extensions (SIMPLE), instant messaging and presence service (IMPS)), and/or short message service (SMS), or any other suitable communication protocols which have not been developed until the filing date of this document.

A driving unit 150 may include, for example, brush-less direct current (BLDC) motors and motor transmissions to provide a driving force that may induce a movement of the device 100 and a physical movement of various devices within the device 100, but is not limited thereto. More specifically, the driving unit 150 can manage a physical movement of the device 100 according to an embodiment, such as a motor, a propeller, a servo, a transmission, an air suction device, and an air exhaust device.

A first and second sensing units (160, 170) may consist of at least one sensor device. In addition, the first and second sensing units (160, 170) may be configured in various forms, such as one or more sensors, one or more memories, one or more microprocessors, digital signal processors (DSPs), application-specific integrated circuits (ASICs), field programmable gate arrays (FPGAs), individual logic circuits, software, hardware, firmware, or any combination thereof.

In addition, the first sensing unit 160 is a sensor that can measure the type of the material introduced into the device 100 and a concentration thereof, and may include at least one selected from a non-dispersive infrared analyzer, a semiconductor gas sensor, a contact combustion gas sensor, an optical gas sensor, a temperature sensor, and a humidity sensor, but the first sensing unit 160 is not limited thereto, but any sensor that can detect the type of gas in the enclosed space 1 and detect the concentration thereof, and any sensor that can detect environmental information (e.g., temperature, humidity, etc.) in the enclosed space 1 can be used.

In addition, the second sensing unit 170 is a gyro sensor and may include an acceleration sensor and a geomagnetic sensor. In addition, the second sensing unit 170 may include at least one selected from a magnetometer, a barometer, a GPS sensor, a rangefinder, an inertial measurement unit (IMU) sensor, and a vision sensor. However, the second sensing unit 170 is not limited thereto, but may be composed of an intelligent sensor capable of detecting spatial information and motion path information, or a known sensor capable performing such functions, or a combination of a plurality of sensors.

The processor 130 may fly, based on sensing information of the second sensing unit 170, for example, based on sensing information of a rangefinder while maintaining a predetermined distance from the water surface. For example, the rangefinder may consist of an ultrasonic sensor, and the height of the device 100 may be detected from the water surface by measuring the time taken for the output ultrasonic wave to be reflected back to the water surface. However, the rangefinder is not limited thereto, but the processor 130 may measure the height of the water level based on the depth information received from the depth gauge, after installing a separate depth gauge in the enclosed space 1, and may also control the height of the device 100 remaining in air, based on the measured height.

The processor 130 can measure the flight state of the device 100 based on the sensing information of the second sensing unit 170. The flight state of the device 100 is defined as a rotational motion state and a translational motion state, and the rotational motion state means a yaw, a pitch, and a roll, while the translational motion state means a longitude, a latitude, an altitude, and a speed. In addition, for example, for the measurement of the rotational motion state, a three-axis gyro sensor, a three-axis acceleration sensor, and a three-axis geomagnetic sensor provided in a second sensing unit 170 may be used; and for the measurement of the translational motion state, the detection results of location information of the GPS sensor and the barometric pressure sensor and/or altimeter provided in the second sensing unit 170 may be used, but the measurement of the rotational motion state and the translational motion state are not limited thereto. Meanwhile, the device 100 located in an enclosed space may have a difficulty in receiving GPS information. Accordingly, for example, the device 100 may detect its current location information in such a method of remembering the route traveled by setting the location of the station 10 as the initial location.

Figure 3:
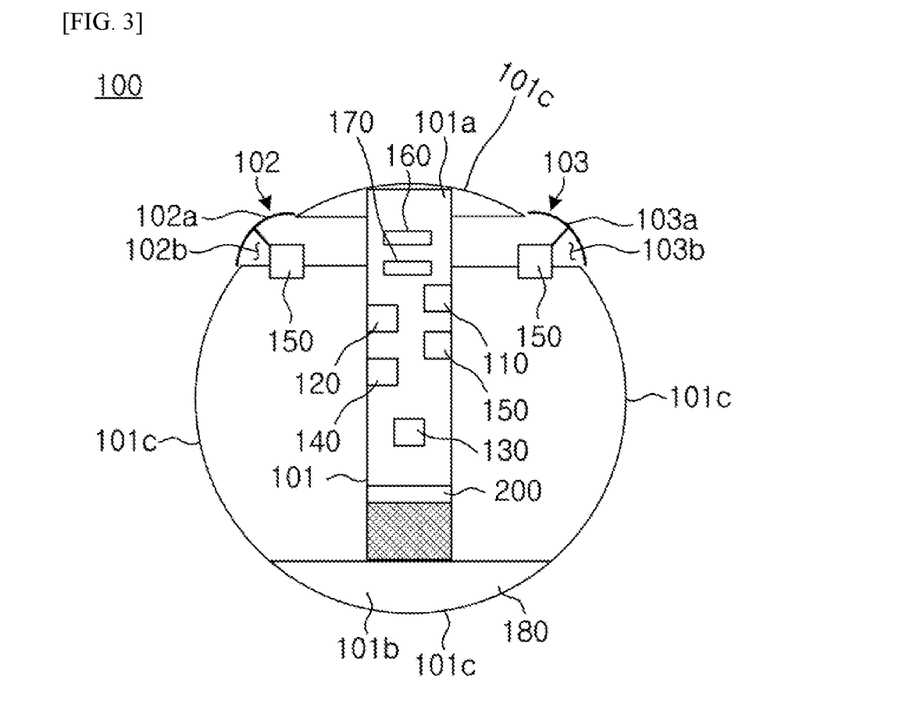
FIG. 3 is an exemplary cross-sectional view of an air state detection floating device capable of remaining in air.

FIG. 3 is an exemplary cross-sectional view of an air state detection floating device capable of remaining in air.

Referring further to FIG. 3, the air state detection floating device capable of remaining in air 100 may include the above-described components of the device 100, that is, a power supply unit 110, a memory 120, a processor 130, a communication unit 140, a driving unit 150, a first sensing unit 160, and a case 101 for accommodating a second sensing unit 170. In addition, the air state detection floating device capable of remaining in air 100 may include a buoyancy supply unit 180, which is installed within the case 101 and provides buoyancy to the device 100.

The appearance of the case 101 may be circular or square in its entirety, but is not limited thereto.

The buoyancy supply unit 180 may be installed at the bottom of the case 101, but is not limited thereto. In addition, the buoyancy supply unit 180 provides a certain level of buoyancy enough to allow the device 100 to float on liquids in the enclosed space 1 and to maintain the device 100 floating in response to an increase or decrease in the water level in the enclosed space 1. In addition, the buoyancy supply unit 180 can provide a certain level of buoyancy enough to allow the device 100 to float on liquids, even when a flight driving device, which will be described later, is installed in the case 101.

For example, the case 101 may be composed of the first case to the third case (101a, 101b, and 101c). The first case 101a can accommodate at least one of the various components constituting the device 100 and prevents the various components from being damaged by an external shock. The buoyancy supply unit 180 may be installed on the second case 101b. In addition, the second case 101b may be coupled to the bottom surface of the first case 101a and maintain a balance of the first case 101a so as to keep the first case 101a in a predetermined position. In addition, the second case 101b may have a hemispherical shape; the upper planar region may be coupled to the bottom surface of the first case 101a; and the lower curved region may face liquids in the enclosed space 1. In addition, the diameter of the top surface of 101b may be greater than that of the back surface of the first case 101a, and accordingly, the second case 101b may support the first case 101a from a lower side thereof and maintain a balance of the first case 101a. However, the second case 101b is not limited to having a hemispherical shape. The third case 101c may be configured to form an appearance of the device 100 in a form surrounding the first and second cases (101a and 101b). The appearance of the third case 101c may have a spherical shape. As the third case 101c has a spherical shape, the liquids can flow down quickly even when the liquids contact the third case 101c. Therefore, the phenomenon that liquids are accumulated in a specific area of the device 100 is prevented.

The first case 101a may be placed past the center of the third case 101c. In addition, the hemispherical shape of the second case 101b may correspond to a part of the region inside the third case 101c. Therefore, the lower curved region of the second case 101b may contact a lower region inside the third case 101c. Each of these first to third cases (101a, 101b, and 101c) may be formed of a plastic material, but is not limited thereto. In addition, the third case 101c may be of a glass material or ceramic-coated with so as to provide corrosion resistance, but is not limited thereto.

In another aspect, each of the first to third cases (101a, 101b, and 101c) may be comprised of an explosion-proof material to minimize damage to the device 100 in the event of an explosion or fire resulting from various flammable materials within the enclosed space 1, but the material is not limited thereto.

In contrast, the shape of each of the first to third cases (101a, 101b, and 101c) and their positional relationship illustrated in the drawings are exemplary and not limited to those illustrated.

In addition, embodiments may be configured such that an air suction device 102 and an air exhaust device 103 are installed in the case 101. In some embodiments, the air suction device 102 and the air exhaust device 103 may be installed on the third case 101c. In addition, the air suction device 102 and the air exhaust device 103 may be located in an upper region of the third case 101c. In addition, the air suction device 102 and the air exhaust device 103 may be installed on some parts among the parts of the area of the case 101 which are not submerged, when the lower part of the case 101 is submerged in the liquid.

A buoyancy supply unit 180 provides buoyancy to the case 101 thereby allowing the case 101 to float in the liquids. In addition, the buoyancy supply unit 180 may include a weight. The weight may be positioned below the first case 101a or may be positioned to correspond to the central region of the second case 101b with respect to the second case 101b. That is, the buoyancy supply unit 180 is located in the center of gravity of the case 101. As a result, the case 101 can remain balanced and float on the liquids. In addition, the lower area of the third case 101c, which is submerged in the liquid, varies depending on the weight of the weight. In addition, all or part of the third case 101c may be submerged in the liquids, and part of the lower region of the first case 101a may be submerged in the liquids.

The first sensing unit 160 may be at least one of various types of sensors, which are classified according to the type of liquid or gas in the enclosed space 1, the materials to be measured, and the degree of accuracy of the measurement. In addition, the first sensing unit 160 may be configured such that the first sensing unit 160 is inserted into the first case 101a and is detachable from the first case 101a. That is, the first sensing unit 160 is attachable to and detachable from the device 100. Accordingly, the air state of the enclosed space 1 can be measured by installing, within the device 100, the first sensing unit 160 equipped with a sensor that meets the characteristics of the enclosed space 1, among the plurality of sensors.

Figure 4:
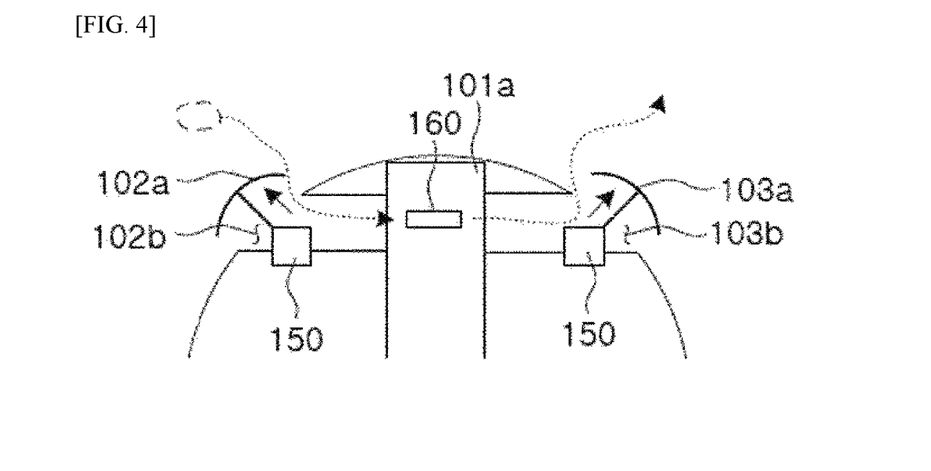
FIG. 4, FIG. 5 and FIG. 6 are diagrams illustrating a driving state of an air suction device and an air exhaust device.
Figure 5:
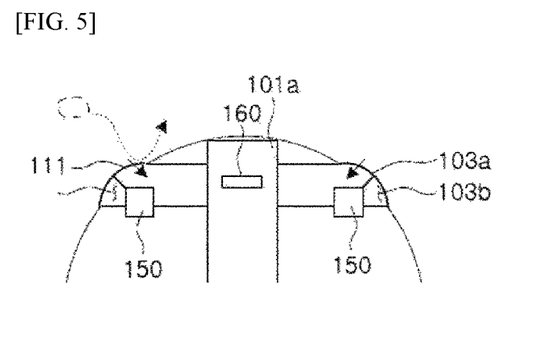
Figure 6:
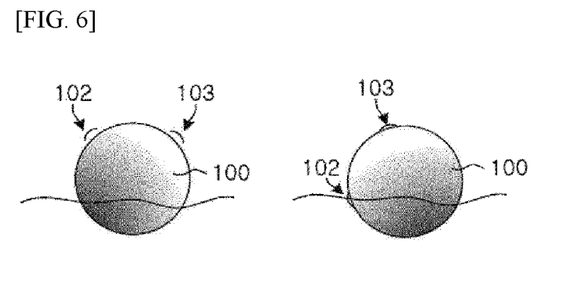

FIGS. 4 to 6 are diagrams illustrating a driving state of an air suction device and an air exhaust device.

Referring further to FIGS. 4 and 5, the driving unit 150 may include a motor associated with driving the air suction device 102 and the air exhaust device 103 based on the control signal of the processor 130. The driving unit 150 moves the air suction cover 102a of the air suction device 102 in the direction of the arrow. In addition, the driving unit 150 moves the air exhaust cover 103a of the air exhaust device 103 in the direction of the arrow.

The processor 130 can transmit control signals for air suction and air exhaust to the driving unit 150 at a predetermined time. In addition, the driving unit 150 opens and closes the air suction cover 102a and the air exhaust cover 103a in response to the control signals received for air suction and air exhaust.

In association with the closing/opening of the air suction cover 102a and the air exhaust cover 103a, when the air suction cover 102a is opened and foreign materials are introduced into the case 101, the first sensing unit 160 can sense the incoming materials. In addition, the gas introduced into the case 101 can be released to the outside of the case 101 by the opening of the air exhaust cover 103a.

In addition, an air suction inlet 102b and an air exhaust outlet 103b may be formed in the case 101. The air suction cover 102a covers the air suction inlet 102b. In addition, the air suction inlet 102b can be opened or closed according to the horizontal movement of the air suction cover 102a in the direction of the arrow. In addition, the air exhaust cover 103a covers the air exhaust outlet 103b. In addition, the air exhaust outlet 103b can be opened or closed according to the horizontal movement of the air exhaust cover 103a in the direction of the arrow.

In addition, when both the air suction inlet 102b and the air exhaust outlet 103b are closed, it is necessary to prevent the introduction of foreign materials into the case 101. Accordingly, the air suction inlet 102b and the air exhaust outlet 103b and the air suction cover 102a and the air exhaust cover 103a may be treated with rubber-packing, respectively, but the treatment is not limited thereto. In addition, an air suction inlet 102b and an air exhaust outlet 103b and an air suction cover 102a and an air exhaust cover 103a may be coated with a liquid-phobic material.

Referring to FIG. 6, when the case 101 corresponds to a preset position based on the detection result from the second sensing unit 170, the processor 130 can detect the degree of contamination in the enclosed space 1 by controlling the driving unit 150 and detecting the air state in the enclosed space 1 together with the air suction and air exhaust operations. For example, the inclination angle information of the case 101 can be detected based on the detection result from the second sensing unit 170. In addition, when the case 101 corresponds to a preset range of angle, the processor 130 can detect the degree of air state together with the air suction and air exhaust operations in the enclosed space 1 by controlling the driving unit 150.

In another aspect, when the device 100 is inclined due to an external factor such as the flow of liquids, the air state detection operation may be stopped. In addition, when the inclination angle corresponds to a preset range of angle, the material introduced can be discharged out of the case 101, by opening the air suction device 102, sensing the air state through the first sensing unit 160, and opening the air exhaust device 103. Accordingly, when the device 100 is inclined at an angle greater than the preset angle due to the movement of the liquids, the introduction of various foreign materials including liquids, etc. into the device 100 can be prevented by closing the air suction inlet 102b and the air exhaust outlet 103b.

In addition, the inclination angle of the device 100 is greater than the preset range of angle by exceeding the preset time period, an abnormal signal can be transmitted to the station 10.

Meanwhile, at least one fan may be installed in the device 100. The operation of the fan may allow for smooth air suction into the air suction inlet 102b and for exhaust of air through the air exhaust outlet 103b.

Figure 7:
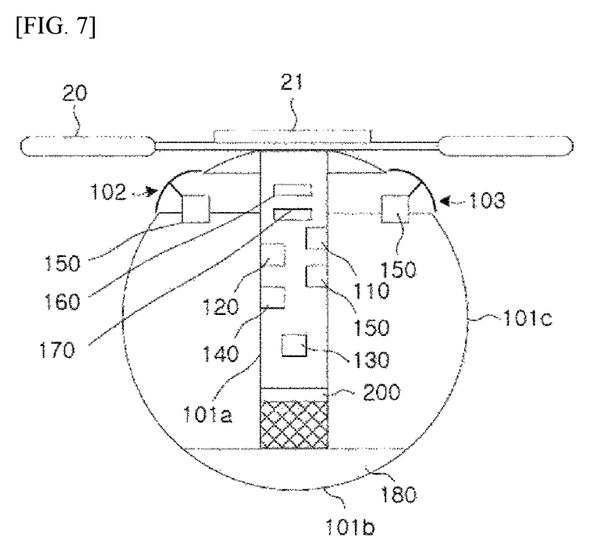
FIG. 7 is an exemplary cross-sectional view of an air state detection floating device capable of remaining in air and a flight driving device coupled thereto according to an embodiment of the present disclosure.
Figure 8:
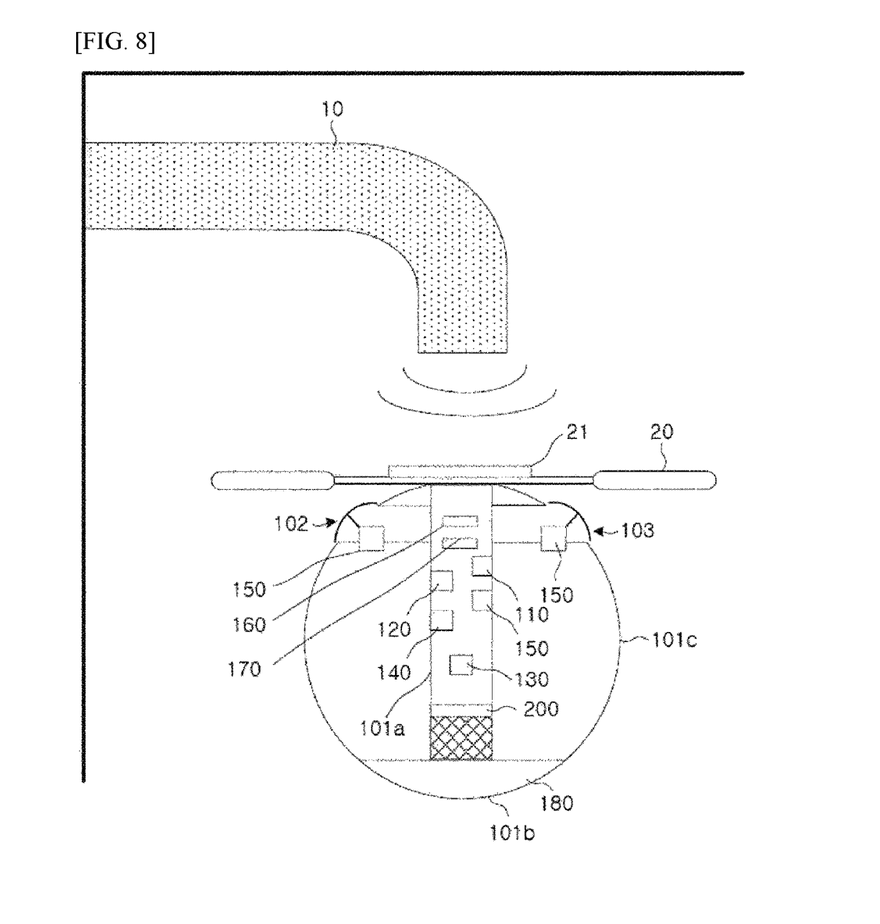
FIG. 8 is a state diagram of a device equipped with a flight driving device before the device is located at a station.
Figure 9:
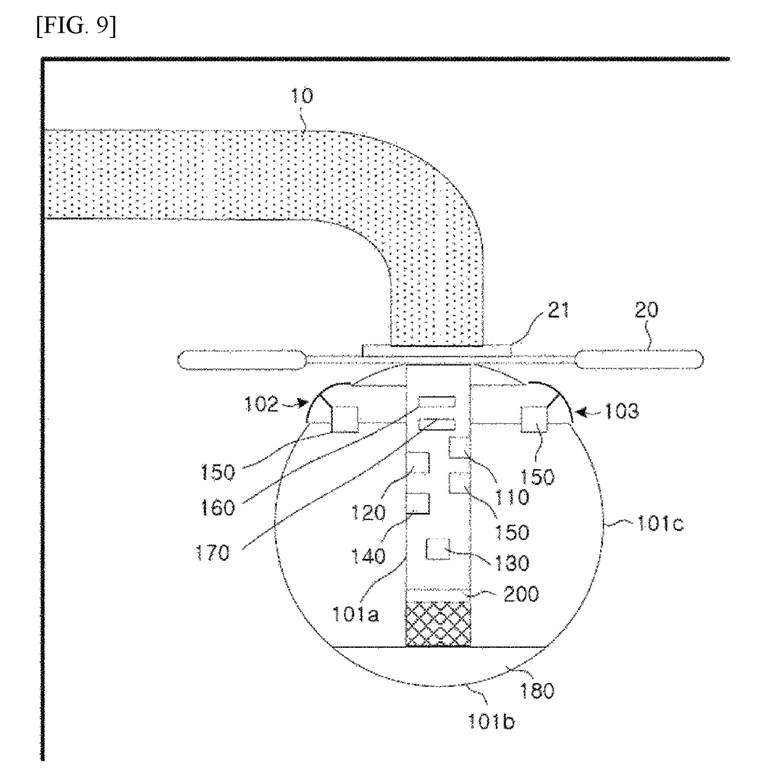
FIG. 9 is a state diagram of a device equipped with a flight driving device when the device is located at a station.
Figure 10:
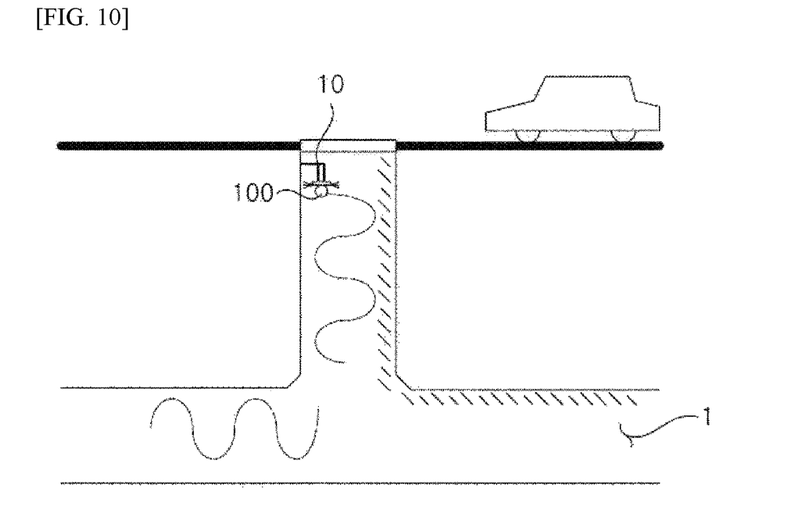
FIG. 10, FIG. 11 and FIG. 12 are exemplary views illustrating a state in which a device equipped with a flight driving device is flying in an enclosed space.
Figure 11:
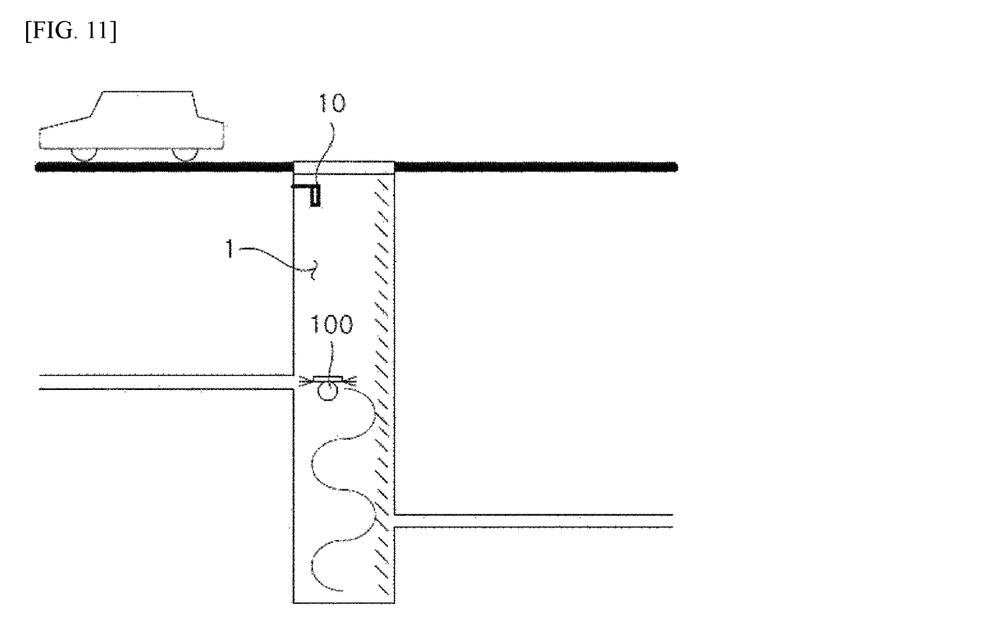
Figure 12:
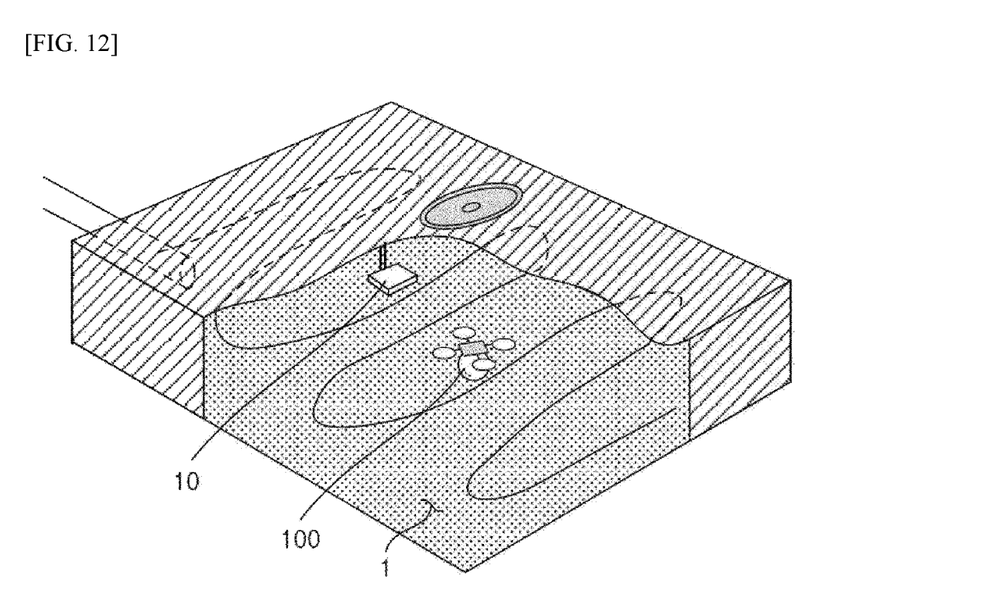

FIG. 7 is an exemplary cross-sectional view of an air state detection floating device capable of remaining in air and a flight driving device coupled thereto according to an embodiment of the present disclosure; FIG. 8 is a state diagram of a device equipped with a flight driving device before the device is located at a station; FIG. 9 is a state diagram of a device equipped with a flight driving device when the device is located at a station; and FIGS. 10 to 12 are exemplary views illustrating a state in which a device equipped with a flight driving device is flying in an enclosed space.

Referring further to FIGS. 7 to 12, a flight driving device 20 may be installed in the air state detection floating device 100 according to an embodiment. The flight driving device 20 may be configured in the form of being attachable to and detachable from the device 100.

The flight driving device 20 may be configured to be able to fly in the air. More specifically, the flight driving device 20 may consist of rotatable wings according to a driving force transmitted from the driving unit 150 of the device 100. In addition, the flight driving device 20 may be configured by a helicopter method or a multi-rotor method, but the method is not limited thereto. In addition, the flight driving device 20 may consist of rotating wing(s) and guard(s) surrounding the wings so as to prevent damage to the flight driving device 20 due to a collision of the device 100, which flies in a narrow area of the enclosed space 1, with the interior wall or other facilities.

The station 10 may be used as a relay device for transmitting and receiving data and providing power, considering that the device 100 has a difficulty in transmitting and receiving data to/from an external monitoring device due to the peculiarity of an enclosed space and that the device 100 has a limitation in receiving power from an external power supply source due to the movement characteristics of the device 100. Such a station 10 may be installed in the upper region in the enclosed space 1. In some embodiments, the station 10 may be installed near an entrance to the enclosed space 1.

The device 100 equipped with the flight driving device 20 may dock with the station 10.

When the device 100 is located at the station 10, the power supply unit 110 may receive the power provided from the station 10 and charge the battery 112.

A magnetic force generating unit 21 may be provided on the flight driving device 20 to induce the device 100 to be positioned at the station 10 in the correct position. In addition, the station 10 may be coated with a magnetic material or a magnet may be installed.

The magnetic force generating unit 21 can take on a magnetic property under the control of the processor 130.

The processor 130 controls the magnetic force generating unit 21 to generate a magnetic force from the magnetic force generating unit 21. Therefore, the docking process of the device 100 with the station 10 can be performed smoothly.

In addition, when device 100 is detached from the station 10, the processor 130 controls the driving unit 150 thereby driving the flight driving device 20. In addition, the processor 130 may control the magnetic force generating unit 21 so that no magnetic force is generated from the magnetic force generating unit 21 and thereby the device 100 may be naturally separated from the station 10.

Meanwhile, although a magnetic force generating unit 21 is illustrated to be provided in the flight driving device 20, the location where magnetic force generating unit 21 is provided is not limited thereto and may be provided on the device 100. In addition, the position and shape of the wing on the flight driving device 20, the location where the magnetic force generating unit 21 is installed, and the shape and location of the station 10 are not limited to those illustrated, and may vary depending on the structures within the enclosed space 1.

The method in which the device 100 equipped with the flight driving device 20 detects an air state while flying within the enclosed space 1 will be described in more detail.

The device 100 may fly in the enclosed space 1, based on the route information previously stored in the memory 120 and its location information detected from the second sensing unit 170. In particular, the pre-stored route information is preset information according to the structure in an enclosed space 1.

In addition, the device 100 may periodically repeat the operation starting from the station 10, which is an initial position, flying in the enclosed space 1 and returning back to the station 10 based on the previously stored route information. In addition, the device 100 may fly within the enclosed space 1 while moving zigzag, but its flying is not limited thereto.

In addition, the device 100 may periodically provide detection information from the first sensing unit 160 to the station 10 during the flight. In addition, the station 10 may transmit the received detection information to an external monitoring device.

In addition, while the device 100 is flying in the enclosed space 1 or while the device 100 is floating in liquids in the enclosed space 1, the processor 130 can continuously or periodically monitor the charging power of the power supply unit 110. In addition, when the charged power is less than the preset value, the processor 130 may set a return path based on path information stored previously. In addition, the processor 130 allows the return flight of the device 100 by controlling the driving unit 150 based on the return path. In addition, upon completion of the docking of the device 100 with the station 10, the device 100 can receive power from the station 10.

In another aspect, the station 10 may receive a movement command signal from an external monitoring device and transmit it to the device 100. The device 100 may fly within the enclosed space 1 or float on liquids based on the movement command signal transmitted from the station 10 and detect an air state therein.

Figure 13:
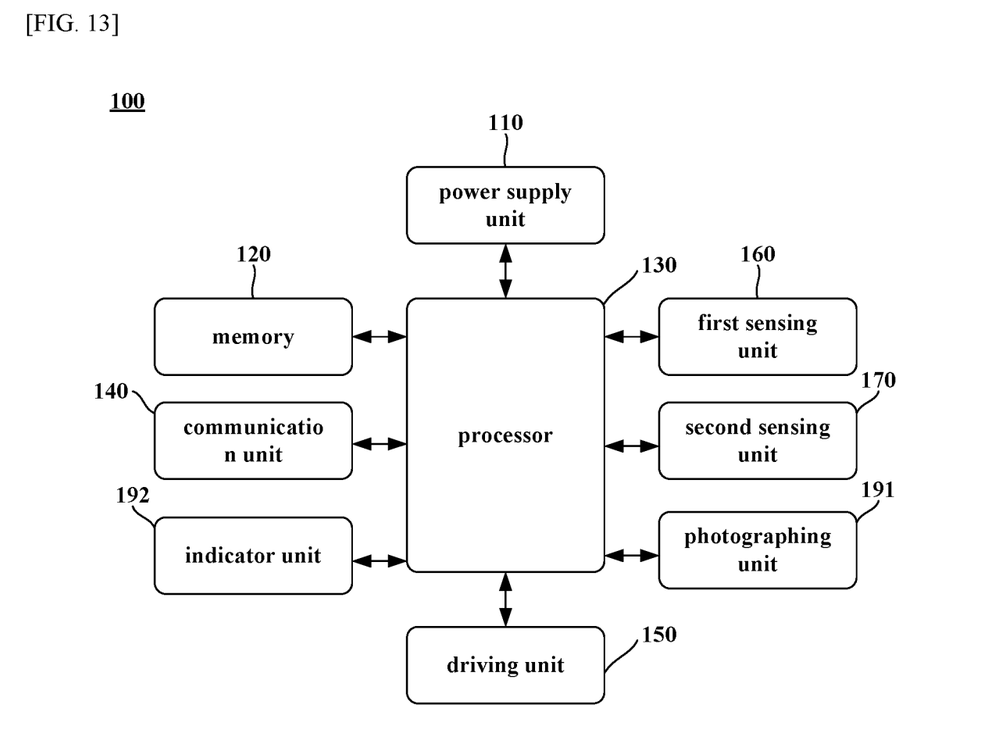
FIG. 13 is a block diagram of an air state detection floating device capable of remaining in air according to another embodiment of the present disclosure.

FIG. 13 is a block diagram of an air state detection floating device capable of remaining in air according to another embodiment of the present disclosure.

Referring further to FIG. 13, the air state detection floating device 100 capable of remaining in air according to another embodiment of the present disclosure may further include a photographing unit 191 and an indicator unit 192.

Software components stored in the memory 120 may include a camera module (or a set of program commands). The camera module is executable by the processor 130 to allow the processor 130 to perform operations, and the operations allow the photographing unit 191 to photograph the interior of the enclosed space 1 and transmit the photographed image to an external monitoring device. In addition, the administrator can check the image of the inside of the enclosed space 1 through the monitoring device. In another aspect, the photographing unit 191 may be activated to photograph the interior of the enclosed space 1, in response to receiving a photographing request signal from the monitoring device.

The indicator unit 192 may be a display device and/or a speaker device. In another aspect, the indicator unit 192 may further include a light supply device.

In addition, the software components stored in the memory 120 may include a display control module (or a set of program commands). The display control module may be executable by the processor 130 to allow the processor 130 to perform operations, and the operations allow the display device to display a variety of information, such as displaying air state information, displaying information received from the monitoring device, displaying the current battery charge status, etc. In another aspect, the operations allow the speaker device to display an acoustic alarm based on the detected air state information. In addition, the auditory alarm may be in various forms. For example, the volume of the audible alarm or the output sound source may vary depending on the danger level of the air state inside the enclosed space 1. Therefore, workers located inside the enclosed space 1 can rapidly obtain information about the air state through the audible alarm and can make a preliminary determination on the possibility of advent of the fatal danger situation.

Figure 14:
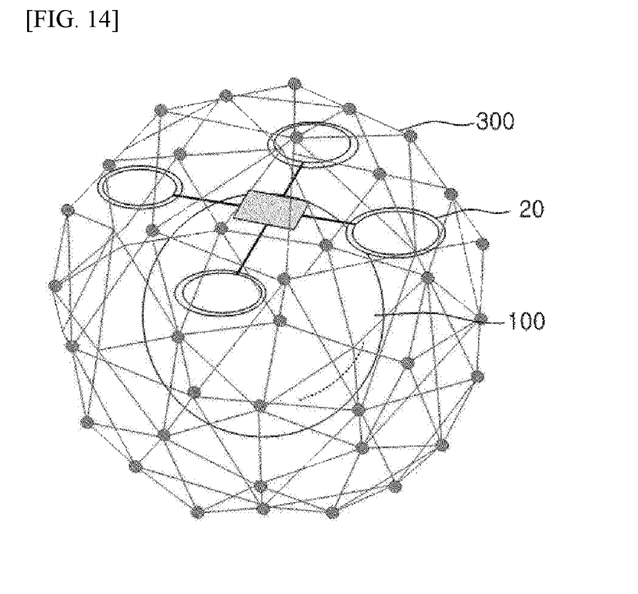
FIG. 14 and FIG. 15 are exemplary views illustrating an air state detection floating device capable of remaining in air according to still another embodiment of the present disclosure.
Figure 15:
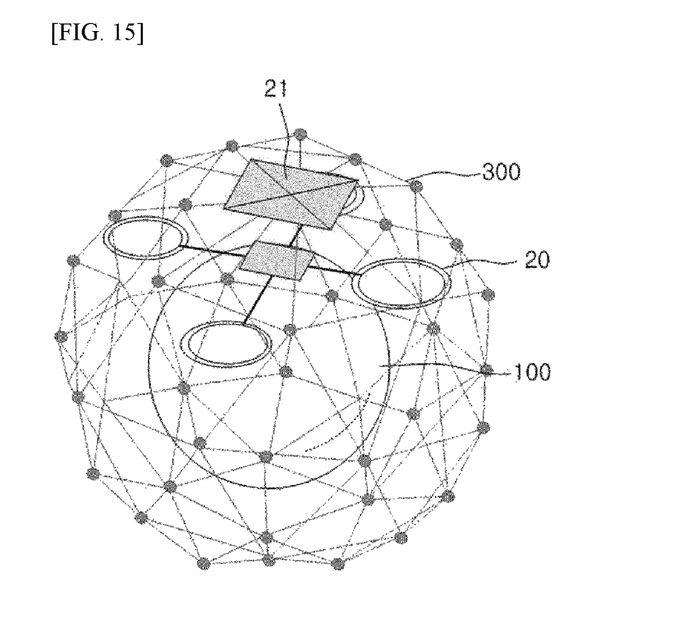

FIGS. 14 and 15 are exemplary views illustrating an air state detection floating device capable of remaining in air according to still another embodiment of the present disclosure.

Referring to FIG. 14, the air state detection floating device 100 capable of remaining in air according to still another embodiment of the present disclosure may be configured to further install a protective case 300.

The protective case 300 may be configured to surround both the device 100 and the flight driving device 20 coupled to the device 100 so that the protective case 300 may be coupled to the device 100. In addition, the protective case 300 may be configured in a form which is attachable to and detachable from the device 100.

The protective case 300 may be configured in a mesh type so that the protective case 300 does not disturb the air flow for smooth driving of the flight driving device 20, and protect the device 100 and the flight driving device 20 from collisions with interior walls or other facilities within the enclosed space 1.

According to FIG. 14, the protective case 300 is illustrated in a circular shape but the shape is not limited thereto, and may have various shapes depending on the coupling relationship between the device 100 and the flight driving device 20 and their overall shapes.

Referring to FIG. 15, the magnetic force generating unit 21 may be installed in the protective case 300. As described above, the magnetic force generating unit 21 may induce the device 100 to be positioned at the station 10. The magnetic force generating unit 21 may be connected directly to the device 10 or via the flight driving device 20, and may be driven under the control of the processor 130.

The processor 130 can control the magnetic force generating unit 21 so that a magnetic force is generated from the magnetic force generating unit 21. Therefore, the docking process between the device 100 and the station 10 can be performed smoothly.

Embodiments according to the present disclosure described above may be implemented in the form of program commands that can be executed through various computer components and recorded in computer-readable recording media. The computer-readable recording media may include program instructions, data files, data structures, etc. alone or in combination. The program instructions recorded on the computer-readable recording media may be specially designed and configured for the present disclosure, or may be known and available to those skilled in the computer software field. Examples of the computer-readable recording medium may include hardware devices specifically configured to store and execute program instructions, such as magnetic media (e.g., hard disks, floppy disks and magnetic tapes, optical recording media (e.g., CD-ROMs and DVDs), and magneto-optical media (e.g., floptical disks, and ROM, RAM, flash memory, etc.). Examples of the program instructions include not only machine codes generated by compilers, but also high-level language codes that can be executed by a computer using an interpreter, etc. Hardware devices may be modified with one or more software modules to perform the processing according to the present disclosure, and vice versa.

Specific implementations described in the present disclosure are exemplary embodiments and do not limit the scope of the present disclosure in any way. For brevity of description, descriptions of conventional electronic configurations, control systems, software, and other functional aspects of the systems may be omitted. In addition, the connections of the lines between the components or connecting members illustrated in the drawings are exemplary functional connections and/or physical or circuit connections, and in real devices, they may be represented as replaceable or additional various functional connections, physical connections, or circuit connections. In addition, unless otherwise specified as in "essential", "important", etc., it may not be a necessary component for the application of the present disclosure.

In addition, although the present disclosure has been described with reference to preferred exemplary embodiments thereof in the Detailed Description of the present disclosure, those skilled in the art or having knowledge in the art will appreciate that various modifications and substitutions are possible without departing from the concepts and technical areas of the present disclosure to be disclosed in the accompanying claims. Accordingly, the technical scope of the present disclosure should not be limited to the details described in the specification, but should be defined by the claims.

INDUSTRIAL APPLICABILITY

The present disclosure can be used in technical fields for detecting contamination materials in an enclosed space.

Effects of the Present Disclosure

An embodiment according to the present disclosure can prevent accidents by detecting an air state in an enclosed space while flying over the enclosed space.

In addition, an embodiment according to the present disclosure can monitor the entire area of an enclosed space by minimizing dead zones where air state measurements are difficult.

An embodiment according to the present disclosure can measure the concentration of contamination on the water surface regardless of the level of liquids in an enclosed space, and can detect the presence of harmful gases and acidity deficiency in the enclosed space thereby being capable of preventing safety accidents.

In addition, an embodiment according to the present disclosure has the advantage in that the power charging and data transmission and reception are possible using a station installed in an enclosed space.

In addition, an embodiment according to the present disclosure can perform an air state sensing operation according to the location information of a device and thereby prevents the problem in that foreign materials are introduced into the device and damage the device.

In addition, an embodiment according to the present disclosure can prevent damage to the device due to collisions with various facilities or the walls of an enclosed space during flight.

What is claimed is:

1. An air state detection floating device capable of remaining in air, which comprises:
a case composed of a first case, a second case, and a third case,
wherein,
the first case includes:
an upper portion including a top surface;
a lower portion including a bottom surface;
a power supply unit;
at least one memory for storing instructions;
at least one processor;
a communication unit for transmitting and receiving data;
a first sensing unit for detecting information on an air state of an enclosed space, wherein the first sensing unit is attachable to and detachable from the first case; and
a second sensing unit for generating location information,
the second case has a hemispherical shape,
the second case comprises an upper surface and a lower surface, wherein the upper surface of the second case has a planar region coupled to the bottom surface of the first case such that the second case supports the bottom surface of the first case, and the lower surface of the second case is a curved surface,
the third case has a spherical shape configured to surround the first case and the second case,
the third case comprises a first portion and a second portion, the second portion of the third case including a lower curved surface coupled to the curved surface of the second case,
the first portion of the third case is coupled to the upper portion of the first case,
the second portion of the third case is coupled to the lower portion of the first case,
the second case includes a buoyancy supply unit for providing buoyancy to the first to the third cases,
a driving unit for generating a driving force is disposed at the second portion of the third case,
a space is formed between the first portion of the third case and the second portion of the third case in an upper area of the first case, and the space is configured to allow a fluid to travel,
an air suction cover and an air exhaust cover are disposed at a region of the space so as to open or close the space and each of the air suction cover and the air exhaust cover is connected to the driving unit,
the instructions are executable by the processor such that the processor performs operations,
the operations comprise an operation that generates a control signal for movement in an enclosed space based on the data; and
an operation that controls the driving unit based on the control signal such that the air suction cover and the air exhaust cover open or close the space.

2. The air state detection floating device of claim 1,
wherein the communication unit transmits and receives the data with a station installed in the enclosed space, and the power supply unit receives power from the station.

3. The air state detection floating device of claim 2,
wherein the operations further comprise:
an operation, which monitors charging power of the power supply unit;
an operation, which sets a return path based on preset route information when the charging power is lower than the preset value;
an operation, which controls the driving unit based on the return path; and
an operation, which is docking with the station and charges the power supply unit using the power received from the station.

4. The air state detection floating device of claim 3,
wherein, at the time of docking with the station, a magnetic force formed in the station is used.

5. The air state detection floating device of claim 1,
wherein the operations further comprise an operation which controls the first sensing unit of the first case based on the detection results of the second sensing unit of the first case.

6. The air state detection floating device of claim 1, which further comprises a flight driving device which is controlled by the driving unit and is attachable to and detachable from the case.

7. The air state detection floating device of claim 6, which further comprises a protective case that surrounds the air state detection floating device capable of remaining in air, and is coupled to the air state detection floating device capable of remaining in air, wherein the protective case has a mesh-type structure.

8. The air state detection floating device of claim 1,
wherein the operations further comprise an operation, which generates a control signal based on a path information, that is previously recorded in the memory and responds to a spatial information in the enclosed space, and thereby controls the driving unit.

* * * * *